US009968927B2

(12) United States Patent
Liu et al.

(10) Patent No.: US 9,968,927 B2
(45) Date of Patent: May 15, 2018

(54) OPTICAL BIOSENSOR DEVICE

(71) Applicant: Taiwan Semiconductor Manufacturing Co., Ltd., Hsin-Chu (TW)

(72) Inventors: Yi-Shao Liu, Hsin-Chu (TW); Emerson Cheng, Hsin-Chu (TW); Yi-Hsien Chang, Hsin-Chu (TW); Chun-Ren Cheng, Hsin-Chu (TW); Ching-Ray Chen, Hsin-Chu (TW); Alex Kalnitsky, San Francisco, CA (US); Allen Timothy Chang, Hsin-Chu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 0 days. days.

(21) Appl. No.: 14/719,991

(22) Filed: May 22, 2015

(65) Prior Publication Data
US 2016/0341656 A1    Nov. 24, 2016

(51) Int. Cl.
| | | |
|---|---|---|
| *H01L 27/12* | (2006.01) | |
| *G01N 27/414* | (2006.01) | |
| *G01N 21/64* | (2006.01) | |
| *B01L 3/00* | (2006.01) | |

(52) U.S. Cl.
CPC .............. *B01L 3/50* (2013.01); *G01N 21/648* (2013.01); *G01N 21/6454* (2013.01); *G01N 27/414* (2013.01); *H01L 27/1203* (2013.01); *H01L 27/1211* (2013.01); *G01N 21/6428* (2013.01); *G01N 2021/6482* (2013.01)

(58) Field of Classification Search
CPC . A61B 10/007; B01L 3/5021; G01N 21/0303; G01N 21/6428; G01N 21/6486; H01L 27/14685; H01L 27/14689
USPC ............................................... 422/548, 82.11
See application file for complete search history.

(56) References Cited

U.S. PATENT DOCUMENTS

| | | |
|---|---|---|
| 5,369,246 A | 11/1994 | Nanos |
| 7,666,285 B1 | 2/2010 | Cho |
| 7,728,401 B2 | 6/2010 | Takatori |
| 8,405,169 B2 | 3/2013 | Cheng et al. |
| 8,569,808 B1 | 10/2013 | Chen et al. |

(Continued)

OTHER PUBLICATIONS

Jang, et al. "Performance Enhancement of Capacitive-Coupling Dual-Gate Ion-Sensitive Field-Effect Transistor in Ultra-Thin-Body." Scientific Reports, 4: 5284. Published Jun. 13, 2014.

(Continued)

*Primary Examiner* — Neil N Turk
(74) *Attorney, Agent, or Firm* — Eschweiler & Potashnik, LLC (57) ABSTRACT

The present disclosure relates to an integrated chip having an integrated optical bio-sensor, and an associated method of fabrication. In some embodiments, the integrated optical bio-sensor has a sensing device arranged within a semiconductor substrate. An optical waveguide structure is located over a first side of the semiconductor substrate at a position over the sensing device. A dielectric structure is disposed onto the optical waveguide structure at a position that separates the optical waveguide structure from a sample retention area configured to receive a sample solution.

20 Claims, 10 Drawing Sheets

(56) References Cited

U.S. PATENT DOCUMENTS

| | | | |
|---|---|---|---|
| 8,728,844 | B1 | 5/2014 | Liu et al. |
| 8,762,925 | B2 | 6/2014 | Chen et al. |
| 8,791,557 | B2 | 7/2014 | Chang et al. |
| 8,846,416 | B1 | 9/2014 | Chu et al. |
| 8,901,003 | B1 | 12/2014 | Pan |
| 9,528,939 | B2 | 12/2016 | Duer |
| 2002/0017916 | A1 | 2/2002 | Costello |
| 2006/0057771 | A1 | 3/2006 | Kovacs |
| 2006/0197118 | A1 | 9/2006 | Migliorato et al. |
| 2007/0210350 | A1 | 9/2007 | Omura |
| 2007/0210807 | A1 | 9/2007 | Arisaka |
| 2008/0063566 | A1 | 3/2008 | Matsumoto |
| 2009/0065761 | A1 | 3/2009 | Chen |
| 2010/0230578 | A1* | 9/2010 | Horikoshi ......... H01L 27/14625 250/208.1 |
| 2010/0248284 | A1 | 9/2010 | Chen |
| 2011/0209555 | A1 | 9/2011 | Ahles |
| 2011/0291873 | A1 | 12/2011 | Shibata |
| 2012/0021918 | A1* | 1/2012 | Bashir ................... B82Y 15/00 506/2 |
| 2012/0032235 | A1 | 2/2012 | Bikumandla |
| 2013/0105868 | A1 | 5/2013 | Kalnitsky et al. |
| 2013/0200438 | A1 | 8/2013 | Liu et al. |
| 2013/0256259 | A1 | 10/2013 | Chang et al. |
| 2013/0293878 | A1* | 11/2013 | Chang ................. G01N 21/6454 356/213 |
| 2013/0307626 | A1 | 11/2013 | Mohammadi |
| 2013/0341734 | A1 | 12/2013 | Merz |
| 2014/0073039 | A1 | 3/2014 | Chang et al. |
| 2014/0134748 | A1 | 5/2014 | Liu et al. |
| 2014/0225166 | A1 | 8/2014 | Ellis-Monaghan et al. |
| 2014/0256030 | A1 | 9/2014 | Shen et al. |
| 2014/0264467 | A1 | 9/2014 | Cheng et al. |
| 2014/0264468 | A1 | 9/2014 | Cheng et al. |
| 2014/0308752 | A1 | 10/2014 | Chang |
| 2014/0335640 | A1 | 11/2014 | Chang et al. |
| 2014/0370636 | A1 | 12/2014 | Dalton et al. |
| 2015/0129937 | A1 | 5/2015 | Chen et al. |
| 2015/0330941 | A1 | 11/2015 | Smith |
| 2017/0018626 | A1 | 1/2017 | Hoffman |

OTHER PUBLICATIONS

Romero-Garcia, et al.; "Silicon Nitride CMOS-compatible Platform for Integrated Photonics Applications at Visible Wavelengths;" Optics Express, vol. 21, No. 12, Jun. 17, 2013, p. 1-11.

Salm, et al. "Ultralocalized Thermal Reactions in Subnanoliter Droplets-in-air;" PNAS; vol. 110; No. 9; Feb. 26, 2013; p. 3310-3315.

"Supporting Information for Ultralocalized Thermal Reactions in Subnanoliter Droplets-in-air;" PNAS, vol. 110; No. 9, Feb. 26, 2013, p. 1-25.

Lee, et al.; "Microchip-based one step DNA Extraction and Real-Time PCR in one Chamber for Rapid Pathogen Identification;" Lab Chip; The Royal Society of Chemistry 2006; p. 886-895.

Dametto, Paolo; "DNA Amplification and Detection Using a pH-Sensing System: Implications for Current Analytical Technologies and Point-of-Care Nucleic Acid Tests;" Aug. 2013; p. 1-31.

Bhattacharya, et al.; "PCR-Based Detection in a Micro-Fabricated Platform;" Lab Chip; The Royal Society of Chemistry; 2008; p. 1130-1136.

Toumazou, et al. "Simultaneous DNA amplification and detection using a pH-sensing semiconductor system." Nature Methods, vol. 10, No. 7, Jul. 2013.

U.S. Appl. No. 13/480,161, filed May 24, 2012.

Mandavifar, et al. "Implementation of a Polysilicon Micro Electro-Thermal Detector in Gas Chromatography System with Applications in Portable Environmental Monitoring." ECS Journal of Solid State Science and Technology, 4 (10) S3062-S3066 (2015). Aug. 28, 2015.

Scorzoni, et al. "Thermal Characterization of a Thin Film Heater on Glass Substrate for Lab-on-Chip Applications." 2014 IEEE International Instrumentation and Measurement Technology Conference (I2MTC) Proceedings. May 12, 2014.

U.S. Appl. No. 15/216,853, filed Jul. 22, 2016.

Non Final Office Action dated Jul. 18, 2016 U.S. Appl. No. 14/713,543.

Notice of Allowance dated Mar. 15, 2017 in connection with U.S. Appl. No. 14/600,315.

Non Final Office Action dated Feb. 14, 2017 U.S. Appl. No. 15/216,853.

U.S. Appl. No. 15/386,545, filed Dec. 21, 2016.

Non-Final Office Action dated Oct. 6, 2017 in connection with U.S. Appl. No. 15/386,545.

Non-Final Office Action dated Jan. 3, 2018 in connection with U.S. Appl. No. 15/216,853.

Petrucci, et al. "Thermal Characterization of Thin Film Heater for Lab-On-Chip Application." 2015 XVIII AISEM Annual Conference. Feb. 2015.

Nanohelix.net RealHelix qPCR Kit. Published in 2009. Retrieved online at http://www.nanohelix,net/02_products/view.asp?pack_code=277.

Non Final Office Action dated Sep. 6, 2016 U.S. Appl. No. 14/600,315.

* cited by examiner

OPTICAL BIOSENSOR DEVICE

BACKGROUND

In recent years, the semiconductor industry has developed integrated chips (ICs) having integrated bio-sensors configured to detect the presence of certain bio-markers in a sample solution (e.g., in a patient's blood). Bio-sensors are analytical devices that convert a biological response into an electrical signal. For example, bio-sensors can generate electrical signals that identify and detect different analytes such as toxins, hormones, DNA strands, proteins, bacteria, etc., in a variety of applications such as molecular diagnostics, pathogen detection, and environmental monitoring. The integration of bio-sensors in system-on-chips (SOCs) provides for promising avenues in the development of diagnostic tools for infectious diseases and cancers.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Various types of bio-sensors have been developed to detect an analyte within a sample solution. Electrical bio-sensors contain sensing devices that can be used for electrical detection of analytes within a solution. For example, bio-molecules such as proteins or DNA (Deoxyribonucleic acid) inherently possess charges, which allow for a transistor to detect the bio-molecules when they are brought into electrical contact with a gate of a transistor device. Alternatively, optical bio-sensors allow for bio-molecules to be detected through optical signals.

Optical bio-sensors typically have a photodetector disposed within a semiconductor substrate. During operation, an analyte with a fluorescent dye can be excited by an excitation element (e.g., a laser). Once excited, the fluorescent dye produces an optical response that is proportional in magnitude and/or frequency to a concentration of an analyte. The optical response can be detected by the photodetector, thereby indicating the presence of the analyte. However, within a system-on-a-chip (SOC), optical bio-sensors are generally unpractical, since the form factor of the SOC will be bulky (i.e., large) due to the large number of components used to implement the bio-sensor.

Accordingly, the embodiments of present disclosure relates to an integrated chip having an integrated optical bio-sensor with a relatively small form factor, and an associated method of fabrication. In some embodiments, the integrated bio-sensor comprises a sensing device disposed within a backside of a semiconductor substrate. An optical waveguide structure is disposed within a dielectric material arranged over the backside of the semiconductor substrate. The dielectric material extends over the optical waveguide structure to a position that separates the optical waveguide from a sample retention area configured to receive a sample solution. The structure of the optical bio-sensor allows for optical detection of an analyte using an integrated bio-sensor having a relatively small form factor that can be easily integrated within a system-on-a-chip (SOC).

Figure 1:
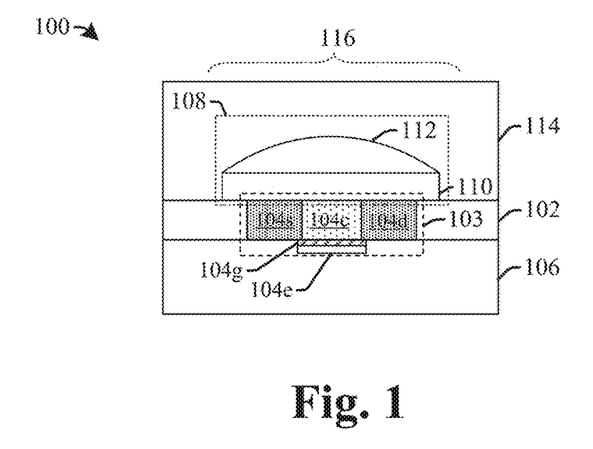
FIG. 1 illustrates a cross-sectional view of some embodiments of an integrated optical bio-sensor.

FIG. 1 illustrates a cross-sectional view of some embodiments of an integrated optical bio-sensor 100 configured to perform optical bio-sensing of an analyte.

The integrated optical bio-sensor 100 comprises a sensing device 103 arranged within a semiconductor substrate 102. In some embodiments, the sensing device 103 may comprise a transistor device having a source region 104s and a drain region 104d separated by a channel region 104c. A gate region is disposed over the channel region 104c at a position laterally between the source region 104s and the drain region

104d. The gate region comprises a gate electrode 104e that is separated from the channel region 104c by a gate dielectric layer 104g.

In some embodiments, the semiconductor substrate 102 may comprise an SOI substrate having an active semiconductor layer. The active semiconductor layer is disposed between an inter-level dielectric (ILD) layer 106 comprising one or more metal interconnect layers (not shown) and a dielectric structure 114 comprising an optical waveguide structure 108. A sample retention area 116 configured to receive a sample solution is located over a top surface of the dielectric structure 114. In some embodiments, the sample retention area 116 may comprise a cavity extending into the dielectric structure 114 and/or a cavity formed by a polymer capping structure located on the dielectric structure 114. The dielectric structure 114 comprises an optically translucent dielectric material that allows for the transmission of optical signals (e.g., photons) from the sample retention area 116 to the sensing device 103.

The optical waveguide structure 108 is disposed between the sensing device 103 and the sample retention area 116. The optical waveguide structure 108 is configured to improve the transmission of an optical signal from the sample retention area 116 to the sensing device 103, thereby enhancing resolution of an optical signal generated by a fluorescent response of an analyte within the sample retention area 116. In some embodiments, the optical waveguide structure 108 may comprise a color filter 110 arranged over the sensing device 103 and a micro-lens 112 arranged over the color filter 110. The micro-lens 112 has a curved top surface abutting the dielectric structure 114 and a substantially flat bottom surface abutting the color filter 110.

Figure 2:
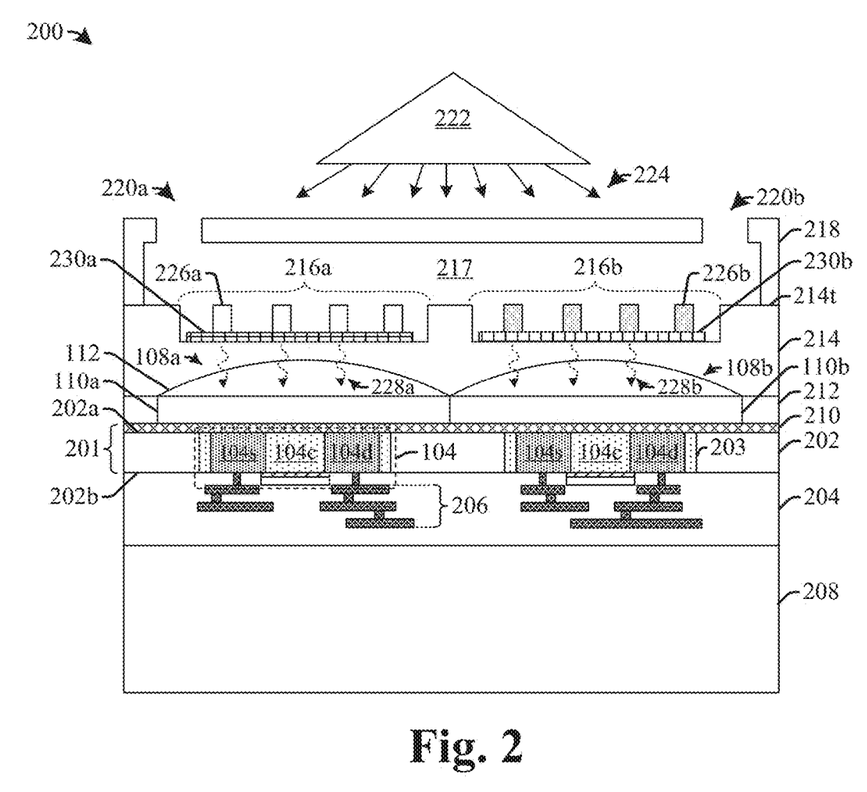
FIG. 2 illustrates a cross-sectional view of some embodiments of an integrated chip comprising integrated optical bio-sensors having optical waveguide structures comprising color filters and micro-lenses.

FIG. 2 illustrates a cross-sectional view of some alternative embodiments of an integrated chip 200 comprising integrated optical bio-sensors configured to perform optical bio-sensing of an analyte.

The integrated chip 200 comprises a semiconductor substrate 201. In some embodiments, the semiconductor substrate 201 may comprise an SOI substrate having an active silicon layer 202 and a buried oxide layer 210 (e.g., a silicon dioxide layer). The active silicon layer abuts the buried oxide layer 210 on a first side 202a and abuts an inter-level dielectric (ILD) layer 204 on a second side 202b, opposing the first side 202a. A handle substrate 208 (e.g., a silicon carrier substrate) abuts a bottom surface of the ILD layer 204. The handle substrate 208 comprises a rigid structure that provides structural support to a remainder of the integrated chip. In some embodiments, the handle substrate 208 may comprise a silicon wafer having a thickness greater than approximately 200 um.

One or more transistor devices 104 are disposed within the active silicon layer 202. The one or more transistor devices 104 have a source region 104s and a drain region 104d having a first doping type (e.g., n-type). A channel region 104c, having a second doping type different than the first doping type, is laterally arranged between the source region 104s and the drain region 104d. In some embodiments, the source region 104s and the drain region 104d may be disposed within a well region 203 having the first doping type with a doping concentration greater than that of the active silicon layer 202. The source region 104s and the drain region 104d extend from the first side 202a of the active silicon layer 202 to the second side 202b of the active silicon layer 202.

The one or more transistor devices 104 are connected to one or more metal interconnect layers 206 disposed within one or more dielectric materials of the ILD layer 204. In some embodiments, the one or more dielectric materials may comprise a low-k dielectric layer, an ultra low-k dielectric layer, an extreme low-k dielectric layer, and/or a silicon dioxide layer. In some embodiments, the one or more metal interconnect layers 206 may comprise conductive contacts configured to connect the transistor devices 104 to metal wires that are vertically interconnected by way of one or more metal vias. In some embodiments, the conductive contacts, the metal vias, and the metal wires may comprise tungsten, copper, and/or aluminum.

A plurality waveguide structures, 108a and 108b, are disposed over the buried oxide layer 210. A dielectric layer 214 is disposed over the plurality waveguide structures, 108a and 108b. In some embodiments, the dielectric layer 214 comprises a plurality of recesses, 216a and 216b, disposed within a top surface 214t of the dielectric layer 214. In some embodiments, the dielectric layer 214 may comprise silicon-dioxide ($SiO_2$). In other embodiments, the dielectric layer 214 may comprise an alternative material such as aluminum oxide, for example. The plurality of recesses, 216a and 216b, are respectively located at a position laterally overlying one of the plurality of waveguide structures, 108a and 108b.

In some embodiments, a capping structure 218 is disposed over the dielectric layer 214. The capping structure 218 forms a micro-fluidic chamber 217 that is in communication with the plurality of recesses, 216a and 216b. The capping structure 218 comprises an inlet port 220a configured to provide fluid into the micro-fluidic chamber 217, and an outlet port 220b configured to output fluid from the micro-fluidic chamber 217. In some embodiments, the capping structure 218 may comprise an optically transparent polymer, such as PDMS (polydimethylsiloxane).

During operation of the integrated chip 200, a sample solution is provided to the micro-fluidic chamber 217. The sample solution may comprise a liquid having one or more target bio-molecules 226a, 226b attached to fluorescent dyes. An excitation element 222 (e.g., laser) is configured to provide incident radiation 224 towards the micro-fluidic chamber 217. When incident radiation 224 strikes the sample solution, the fluorescent dye(s) attached to the one or more target bio-molecules 226a, 226b will provide a fluorescent response in the form of an optical signal comprising photons 228. The plurality waveguide structures, 108a and 108b, transmit the optical signal to the transistor devices 104. When photons 228 from the optical signal strike the semiconductor material of the transistor devices 104, the energy of the photons 228 will cause the photons 228 to knock electrons from the semiconductor lattice, which generates currents in the transistor devices 104. Since the transistor devices 104 are disposed within a back-side of the active silicon layer 202, the photons 228 are able to reach the semiconductor material with a higher energy than that allowable by traditional transistor devices (which may have a gate dielectric overlying an exposed surface of the transistor) so as to increase the current generated in response to the optical signal. In some embodiments, the optical waveguide structures 108 may abut the back-side of the active silicon layer 202 (without the buried oxide layer 210 therebetween), thereby increasing the energy of the photons 228 reaching the transistor devices 104 and the resulting output signal from the transistor devices 104.

In some embodiments, the plurality of waveguide structures, 108a, 108b may respectively comprise a color filter 110 and a micro-lens 112 abutting a top surface of the color filter 110. Different color filters, 110a and 110b, are configured to pass a selected frequency range of an optical signal, while blocking other frequency ranges. For example, a first color filter 110a may allow red light to pass while blocking other wavelengths of light, while a second color filter 110b may allow green light to pass while blocking other wavelengths of light. The color filters 110 allow for the integrated chip 200 to distinguish between different optical signals output by different constituents of a sample solution within the micro-fluidic chamber 217.

For example, a sample solution used in optical detection may label different target bio-molecules with different fluorescent dyes configured to generate photons having different energies (i.e., wavelengths). Furthermore, to detect different analytes within a sample solution, different probes, 230a and 230b, attached to different fluorescent dyes may be introduced within the different recesses, 216a or 216b. When a sample solution is provided to the micro-fluidic chamber 217, if present, a target bio-molecule 226a, 226b will be immobilized by an associated probe 230a, 230b. In general, the target bio-molecule 226a, 226b is labeled with fluorescent dye having a first color that is different than a second color of a fluorescent dye attached to a probe 230. When incident radiation 224 strikes the sample solution, the fluorescent dyes of the probes 230a, 230b and the target bio-molecules 226a, 226b will provide a fluorescent response in the form of an optical signal comprising photons having different frequencies (respectively corresponding to a particular analyte). The color filters 110 enable the integrated chip 200 to differentiate between different target bio-molecules, 226a and 226b, and/or between a target bio-molecule 226a, 226b and a probe 230 by distinguishing between optical signals. In some embodiments, a first color may enable the integrated chip 200 to determine if a correct probe is present to detect a target bio-molecule, while a second color may enable the integrated chip 200 to determine if the bio-molecule is present.

Respective micro-lenses 112 are aligned laterally with the individual color filters 110a, 110b and overlie a transistor device 104. The micro-lenses 112 are configured to focus the optical signal towards the transistor device 104. By focusing the optical signal toward the transistor device 104, the optical signal can be amplified to improve sensing. In some embodiments, the micro-lens 112 may comprise photoresist or an oxide. The micro-lens 112 may have an index of refraction smaller than the index of refraction of the color filters 110a, 110b. In various embodiments, the micro-lenses 112 may have a curvature configured to focus the optical signal onto a center of an underlying transistor device 104.

In some embodiments, to further improve the optical signal received by the transistor devices 104, the color filters 110 may be surrounded by a dielectric material 212 having a higher (i.e., larger) index of refraction than a material of the color filter 110. This allows for the dielectric material 212 to act as a sidewall waveguide structure that improves transmission (e.g., reflectance and refraction of incident radiance) of the optical signal.

Although integrated optical bio-sensors of FIGS. 2-6 are illustrated as having two transistor/sensing devices, it will be appreciated that the disclosed integrated optical bio-sensors may comprise a large array of transistor/sensing devices, in some embodiments. For example, a disclosed integrated optical bio-sensor may comprise a 100×100 array of transistor/sensing devices. The array of transistor/sensing devices may be divided into different areas by applying different probes to the different areas to detect different diseases (e.g., breast cancer, liver cancer, etc.) or different nucleotides of a DNA strand (e.g., A, T, C, G) from a same sample. For example, a 100×100 array of transistor/sensing devices may be divided into 10 sub-arrays respectively comprising 10×10 sub-arrays of transistor/sensing devices. Dividing a larger array of transistor/sensing devices into a plurality of sub-arrays allows for the integrated optical bio-sensor to do multiplex detection. In such embodiments, the color filters 110 allow for the integrated optical bio-sensors to distinguish between different probes and several different targets that will appear in a sample solution.

Figure 3:
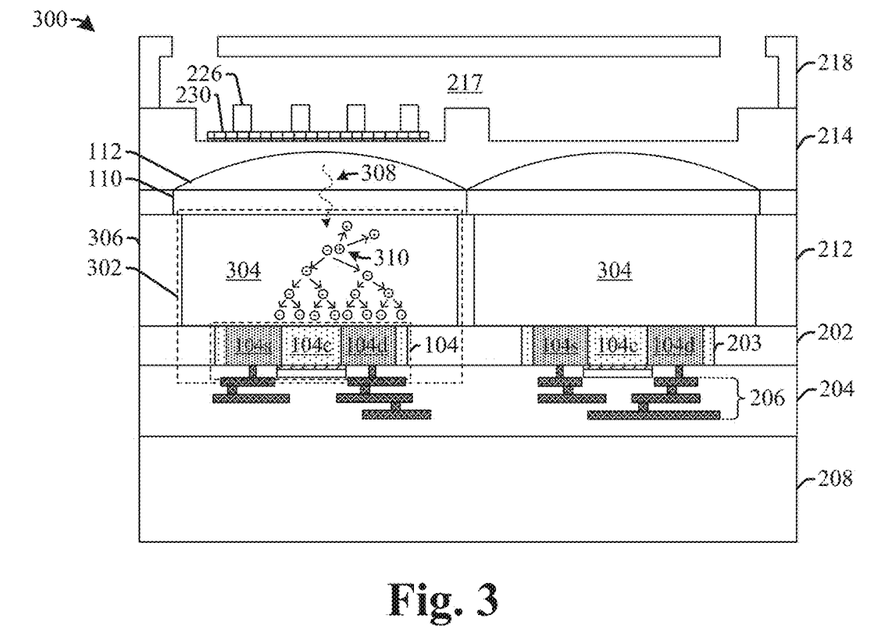
FIG. 3 illustrates a cross-sectional view of some embodiments of an integrated chip comprising integrated optical bio-sensors having a signal enhancement element.

FIG. 3 illustrates some embodiments of an integrated chip 300 having integrated optical bio-sensor comprising a signal enhancement element.

The integrated chip 300 comprises a sensing device 302 having a transistor device 104 and an overlying signal enhancement element 304. The transistor device 104 is disposed within an active silicon layer 202. The signal enhancement element 304 is vertically arranged between the transistor device 104 and a color filter 110. In some embodiments, the signal enhancement element 304 may be arranged within a dielectric layer 306 overlying the active silicon layer 202. The signal enhancement element 304 is configured to receive incident photons 308 from target bio-molecules 226 within the micro-fluidic chamber 217, and based upon the incident photons 306 to generate an enhanced electrical signal that is provided to the transistor device 104.

In some embodiments, the signal enhancement element 304 may comprise a photodiode or an avalanche photodiode. The avalanche photodiode comprises a semiconductor material having a first region with a first doping type (e.g., n-type doping) and an overlying second region (e.g., p-type doping) with a second doping type that is different than the first doping type. In various embodiments, the semiconductor material may comprise silicon (Si), indium gallium arsenide (InGaAs), indium-phosphide (InP), and/or germanium (Ge). During operation, a high reserve bias voltage (e.g., greater than or equal to 50 V) is applied across the avalanche photodiode (e.g., by way of conductive contacts abutting upper and lower surfaces of the avalanche photodiode). When the incident photos 306 strike the avalanche photodiode, electron-hole pairs 308 are generated within the avalanche photodiode. The high reverse bias voltage forms a strong internal electric field, which accelerates the electrons and holes (in opposite directions) through the crystal lattice of the semiconductor material and produces secondary electrons by impact ionization. As electrons collide with other electrons in the semiconductor crystal lattice, the electrons become part of an enhanced photocurrent through avalanche multiplication.

Figure 4A:
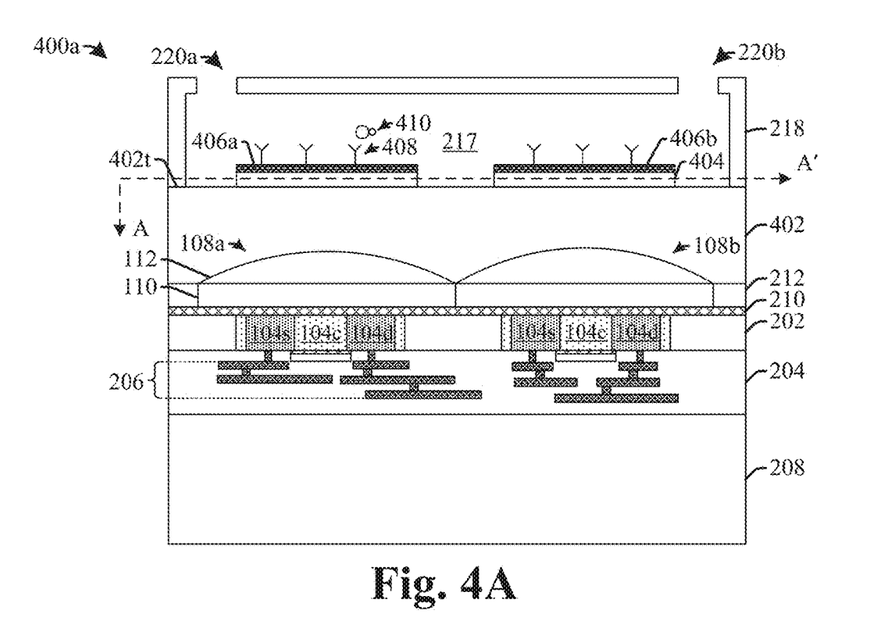
FIGS. 4A-4C illustrate cross-sectional views of some embodiments of an integrated chip comprising integrated optical bio-sensors having optical signal conduits.
Figure 4B:
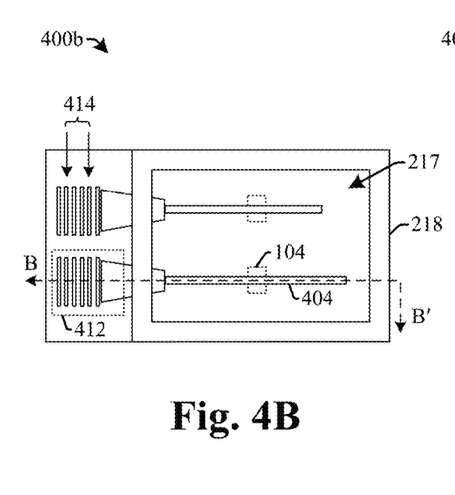
Figure 4C:
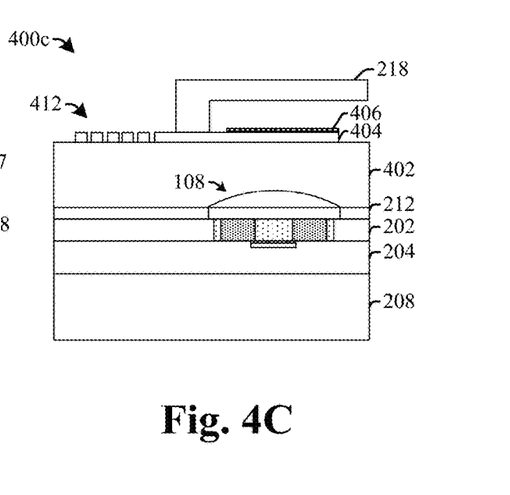

FIGS. 4A-4C illustrate some additional embodiments of an integrated chip comprising integrated optical bio-sensors having one or more optical signal conduits.

FIG. 4A illustrates a cross-sectional view 400a of an integrated optical bio-sensor.

As shown in the cross-sectional view 400a, a dielectric material 402 is disposed over a plurality of optical waveguide structure 108a, 108b. The dielectric material 402 has a substantially flat top surface 402t. One or more optical signal conduits 404 are disposed onto the top surface 402t of the dielectric material 402. In some embodiments, the one or more optical signal conduits 404 may comprise planar waveguides. In some embodiments, the one or more optical signal conduits 404 may have a smooth outer surface, resulting in more efficient transmission of an optical signal.

The one or more optical signal conduits 404 are configured to conduct an optical signal to locations within a micro-fluidic chamber 217 that overlie the plurality of optical waveguide structures 108. Since the one or more optical signal conduits 404 limit the areas to which incident radiation is provided, the one or more optical signal conduits 404 prevent incident radiation from being provided to an entire area of the micro-fluidic chamber 217. The one or more optical signal conduits 404 thereby prevent photobleach (use up fluorescent dye in solution) of a sample solution so as to enable a longer detection time.

In some embodiments, a reception layer 406a, 406b may be disposed over the one or more optical signal conduits 404 in areas vertically overlying the transistor devices 104. The reception layer 406a, 406b comprises receptors 408 configured to attach to a particular type of analyte 410 that are within a sample solution in the micro-fluidic chamber 217. Once the analyte 410 is attached to the reception layer 406a, 406b, light extending out of the one or more optical signal conduits 404 as an evanescent field will excite fluorescent dyes of the analyte 410 attached to the reception layer 406a, 406b. In some embodiments, different reception layers, 406a and 406b, may be disposed on different ones of the one or more optical signal conduits 404. The different reception layers, 406a and 406b, are respectively configured to attach to different analytes so as to allow the transistor devices 104 to detect the different analytes. For example, a first reception layer 406a may attach to an analyte corresponding to a DNA mutation of prostate cancer, while a second reception layer 406b may attach to an analyte corresponding to a DNA mutation of thyroid cancer.

FIG. 4B illustrates a top-view 400b of the integrated chip along line A-A' of cross-sectional view 400a.

As shown in top-view 400b, the one or more optical signal conduits 404 are connected to one or more optical input conduits 412 located outside of the micro-fluidic chamber 217. The one or more optical input conduits 412 are configured to receive an optical signal 414. In some embodiments, the one or more optical input conduits 412 may be a coupling structure, such as a grating coupler, for example. The one or more optical signal conduits 404 convey the optical signal from the one or more optical input conduits 412 outside of the micro-fluidic chamber 217 to an area within the micro-fluidic chamber 217, so that a laser or other light source may be provided remotely. In some embodiments, a waveguide splitter (not shown) may be coupled to an optical input conduits 412, so that the optical input conduits 412 provides light to areas of the micro-fluidic chamber 217 overlying multiple transistor devices 104. FIG. 4C illustrates a cross-sectional view 400c of the integrated chip along line B-B' of cross-sectional view 400b.

Figure 5:
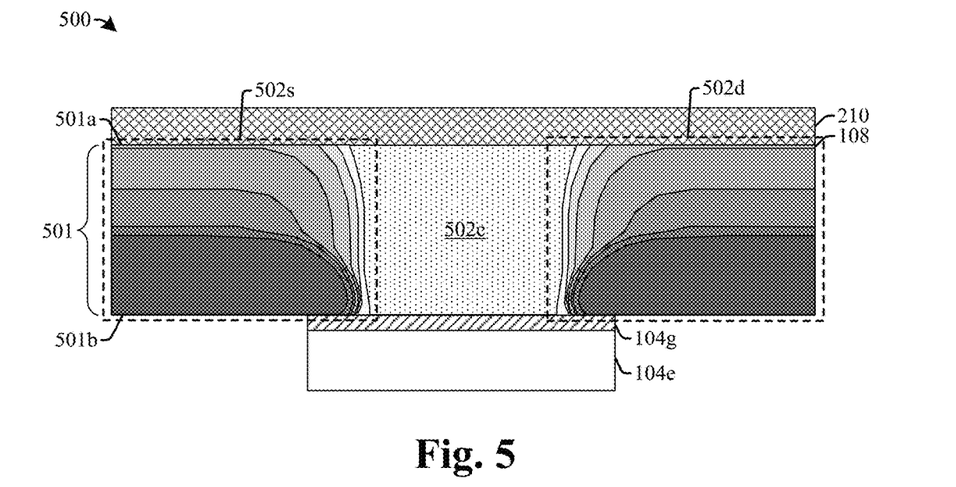
FIG. 5 illustrates a cross-sectional view of some embodiments of a sensing device for an integrated optical bio-sensor comprising a field effect transistor.

FIG. 5 illustrates a cross-sectional view of some embodiments of a sensing device comprising a field effect transistor 500.

Field effect transistor 500 comprises a source region 502s and a drain region 502d disposed within an active semiconductor layer 501. The source region 502s and the drain region 502d are laterally separated by a channel region 502c. The source region 502s and the drain region 502d vertically extend from a first side 501a of the active semiconductor layer 501 to an opposing, second side 501b of the active semiconductor layer 501. By extending through the active semiconductor layer 501, the field effect transistor 500 enables effective sensing from a first side 501a (i.e., a "backside") of the active semiconductor layer 501. For example, incident photons striking the first side 501a of the active semiconductor layer 501 have sufficiently high energies to induce a current (i.e., to knock electrons free from a lattice of the semiconductor material of the active semiconductor layer 501) within the channel region 502c.

In some embodiments, the first side 501a of the active semiconductor layer 501 abuts a buried oxide layer 210. In some embodiments, the second side 501b of the active semiconductor layer 501 abuts a gate dielectric layer 104g. In some embodiments, the source region 502s and the drain region 502d may have a curvature that curves inward as a distance to the first side 501a of the active semiconductor layer 501 decreases. In various embodiments, the source region 502s and the drain region 502d may comprise arsenic dopants or phosphorous dopants. In some embodiments, the source region 502s and the drain region 502d may comprise a graded doping concentration that decreases as a distance from the first side 501a of the active semiconductor layer 501 decreases. In such embodiments, the doping concentration at the first side 501a of the active semiconductor layer 501 may be in a range of between approximately $1e17/cm^3$ and approximately $1e20/cm^3$.

Figure 6:
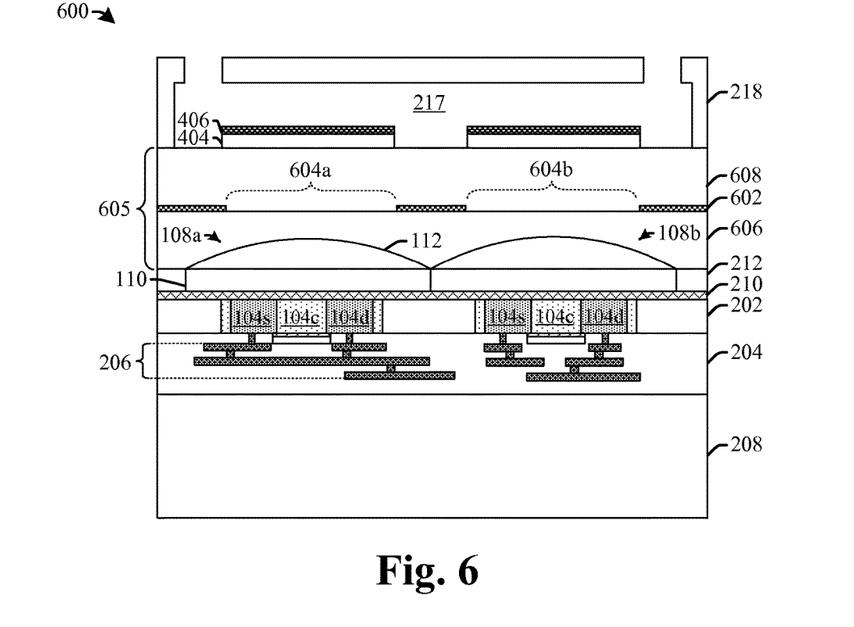
FIG. 6 illustrates a cross-sectional view of some embodiments of an integrated chip comprising integrated optical bio-sensors having one or more electrodes.

FIG. 6 illustrates a cross-sectional view of some embodiments of an integrated chip 600 comprising integrated bio-sensors having one or more electrodes.

The integrated chip 600 comprises one or more electrodes 602 disposed within a dielectric structure 605 overlying the optical waveguide structures 108a, 108b. The dielectric structure 605 comprises a first dielectric layer 606 and a second dielectric layer 608. The first dielectric layer 606 abuts a first side of the one or more electrodes 602 and is vertically arranged between the one or more electrodes 602 and the active silicon layer 202. The second dielectric layer 608 abuts a second side of the one or more electrodes 602 opposite the first side. In some embodiments, the first dielectric layer 606 and the second dielectric layer 608 may comprise a same material (e.g., SiO2). In other embodiments, the first dielectric layer 606 and the second dielectric layer 608 may comprise different materials.

The one or more electrodes 602 comprise a conductive material. In some embodiments, the one or more electrodes 602 may comprise a metal such as aluminum, copper, or a combination thereof. The one or more electrodes 602 are arranged within the dielectric structure 605 in a manner that provides for openings 604a, 604b vertically overlying the optical waveguide structures 108. For example, the electrodes 602 provide a first opening 604a overlying a first optical waveguide structures 108a and a second opening 604b overlying a second optical waveguide structures 108b. The openings 604 allow for light to travel from the optical signal conduits 404 to the optical waveguide structures 108a, 108b.

In some embodiments, the one or more electrodes 602 may be configured to resistively heat a fluid or environment contained in a micro-fluidic chamber 217 to enable heat-mediated bio reactions within a sample solution. In such embodiments, the one or more electrodes 602 may be coupled to a current source (not shown). As energy is dissipated by the conductive material of the one or more electrodes 602, heat is dissipated from the one or more electrodes 602 to heat a sample solution within the micro-fluidic chamber 217.

In some alternative embodiments, the one or more electrodes 602 may be configured to generate an electric field that guides analytes or target bio-molecules by dielectrophoresis (DEP). For example, the one or more electrodes 602 may be configured to generate an electric field that guides analytes or target bio-molecules within the micro-fluidic chamber 217 to a reception layer 406. In some embodiments, the one or more electrodes 602 may be configured to use DEP to manipulate target bio-molecules to positions above the transistor devices 104, thereby intensifying the optical signal output from a sample solution.

Figure 7:
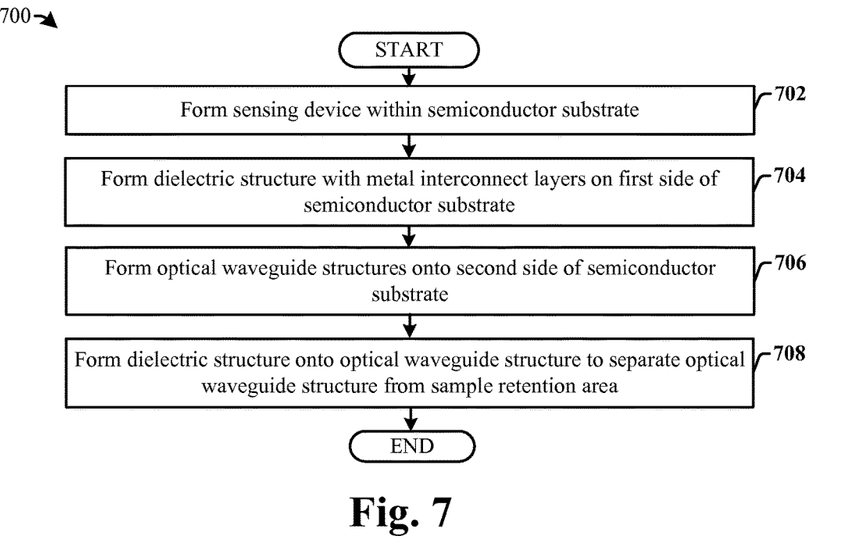
FIG. 7 illustrates a flow diagram of some embodiments of a monolithic manufacturing method of forming an integrated optical bio-sensor.

FIG. 7 illustrates a flow diagram of some additional embodiments of a method 700 of forming an integrated chip comprising an integrated optical bio-sensor.

While disclosed methods (e.g., methods 700 and 800) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 702, a sensing device is formed within a semiconductor substrate. In some embodiments, the sensing device may comprise a transistor device (e.g., a MOSFET). The semiconductor substrate may comprise any type of semiconductor body (e.g., silicon, SiGe, SOI) such as a semiconductor wafer and/or one or more die on a wafer, as well as any other type of semiconductor and/or epitaxial layers associated therewith.

At 704, a dielectric structure comprising a plurality of metal interconnect layers is formed on a first side of the semiconductor substrate.

At 706, one or more optical waveguide structures are formed onto a second side of the semiconductor substrate.

At 708, a dielectric structure is formed onto the optical waveguide structure at a position that vertically separates the optical waveguide structure from a sample retention area configured to receive a sample solution.

Figure 8:
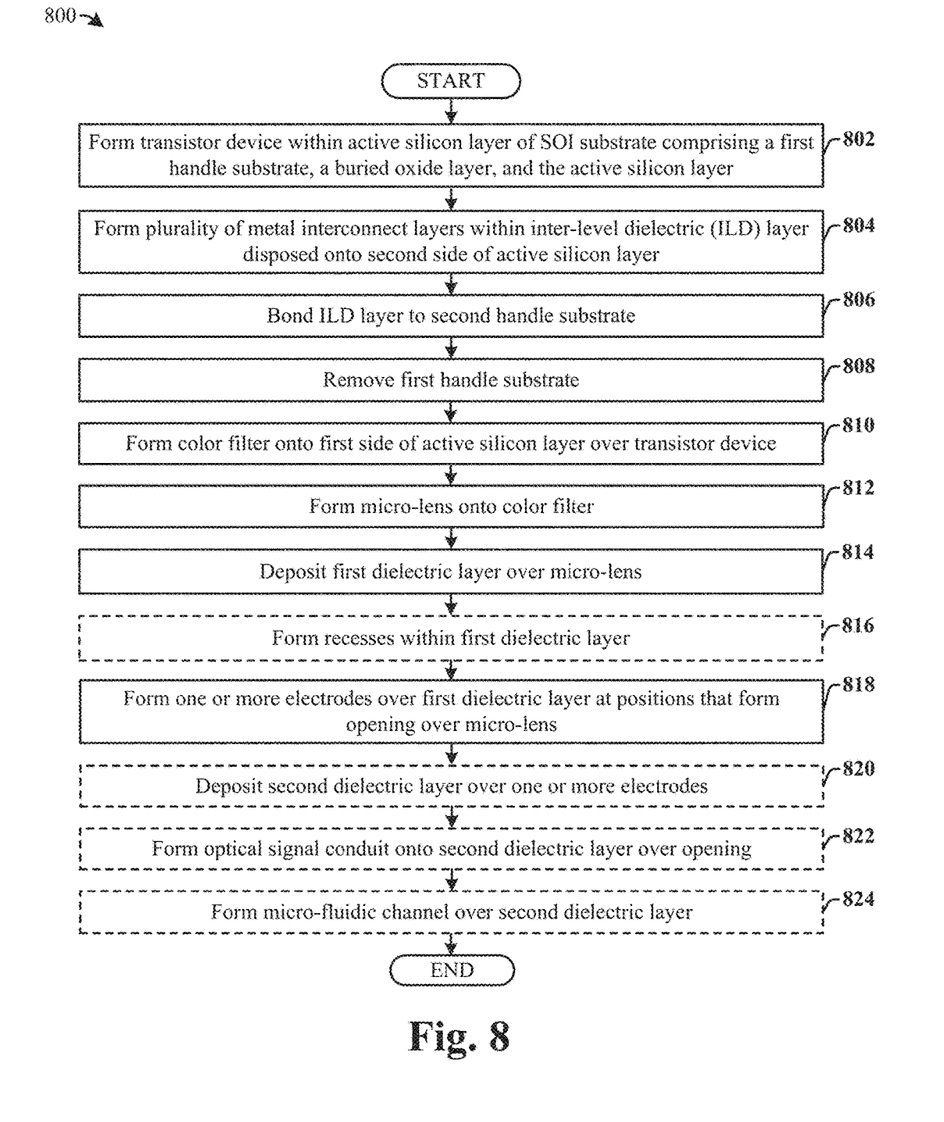
FIG. 8 illustrates a flow diagram of some additional embodiments of a monolithic manufacturing method of forming an integrated optical bio-sensor.

FIG. 8 illustrates a flow diagram of some additional embodiments of a method 800 of forming an integrated chip comprising an integrated optical bio-sensor.

At 802, a transistor device (e.g., a MOSFET, an ISFET, etc.) is formed within an active silicon layer of a silicon-on-insulator (SOI) substrate comprising a first handle substrate, a buried oxide layer, and the active silicon layer.

At 804, a plurality of metal interconnect layers are formed within an inter-level dielectric (ILD) layer formed onto a second side of the active silicon layer. In some embodiments, the ILD layer may comprise one or more dielectric materials.

At 806, the ILD layer is bonded to a second handle substrate.

At 808, the first handle substrate is removed from the first side of active silicon layer. In some embodiments, the buried oxide layer may also be partial or wholly removed from the silicon side of the active silicon layer.

At 810, a color filter is formed onto the first side of active silicon layer over the transistor device.

At 812, a micro-lens is formed over the color filter.

At 814, a first dielectric layer is formed over the micro-lens.

At 816, a recess may be formed within the first dielectric layer over the micro-lens, in some embodiments.

At 818, one or more electrodes may be formed over the first dielectric layer, in some embodiments. The one or more electrodes are formed at positions that form an opening over the micro-lens.

At 820, a second dielectric layer is formed over the one or more electrodes and over the first dielectric layer.

At 822, an optical signal conduit is formed onto the second dielectric layer over the opening.

At 824, a micro-fluidic chamber is formed over the second dielectric layer. In some embodiments, the micro-fluidic chamber may be formed by forming a capping layer onto the second dielectric layer. In other embodiments, the micro-fluidic chamber may be formed by forming channel structures over the second dielectric layer to form a sensing well (e.g., a recess having sidewalls but no overlying upper surface)

FIGS. 9-17 illustrate some embodiments of cross-sectional views showing a method of forming an integrated chip comprising an integrated bio-sensor having a color filter disposed over a sensing device. Although FIGS. 9-17 are described in relation to method 800, it will be appreciated that the structures disclosed in FIGS. 9-17 are not limited to such a method, but instead may stand alone as structures independent of the method.

Figure 9:
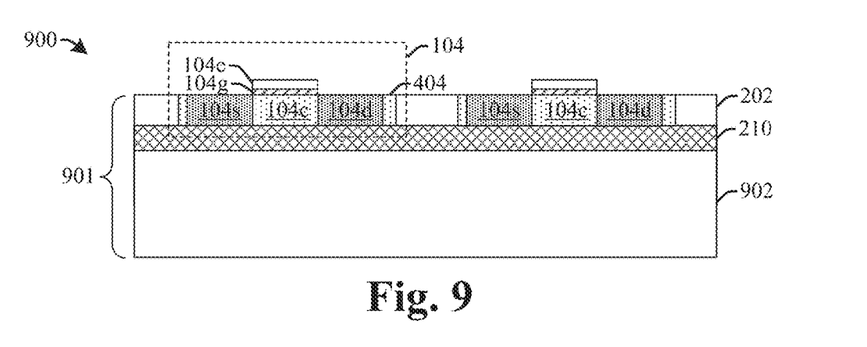
FIGS. 9-17 illustrate some embodiments of cross-sectional views showing a method of forming an integrated chip comprising an integrated optical bio-sensor having an optical waveguide structure arranged over a transistor device.

FIG. 9 illustrates some embodiments of a cross-sectional view 900 of an integrated chip corresponding to act 802.

As shown in cross-sectional view 900, a transistor device 104 is formed within an active silicon layer 202 of a SOI semiconductor substrate 901. In some embodiments, the SOI substrate may comprise the active silicon layer 202, which is separated from an underlying first handle substrate 902 by a buried oxide layer 210. In some embodiments, the transistor device 104 may comprise a MOSFET having a source region 104s, a drain region 104d that is separated from the source region 104s by a channel region 104c, and a gate region comprising a gate electrode 104e separated from the channel region 104c by a gate dielectric layer 104g. The source region 104s and the drain region 104d may be formed by implanting dopant species (e.g., boron or phosphorus) into the active silicon layer 202 at a high energy. In some embodiments, the dopants may be subsequently driven into the active silicon layer 202 using a high temperature anneal. Implanting dopant species into the active silicon layer 202 is performed so that the source region 104s and the drain region 104d vertically extend through the active silicon layer 202 to the buried oxide layer 210. The gate region is formed over the channel region 104c by deposition processes and one or more subsequent patterning processes.

Figure 10:
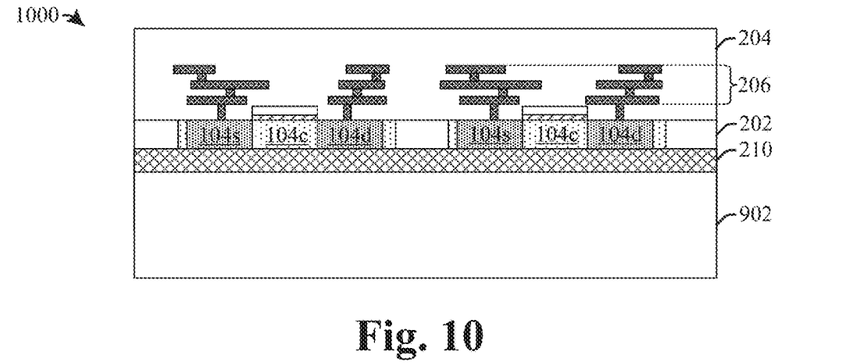

FIG. 10 illustrates a cross-sectional view 1000 of an integrated chip corresponding to act 804.

As shown in cross-sectional view 1000, an inter-level dielectric (ILD) layer 204 comprising one or more dielectric materials is formed onto the active silicon layer 202. A plurality of metal interconnect layers 206 are formed within the ILD layer 204. The ILD layer 204 may comprise one or more of a low-k dielectric layer, an ultra-low-k dielectric layer, and/or an oxide layer. In some embodiments, the ILD layer 204 may be deposited by way of a vapor deposition technique (e.g., physical vapor deposition, chemical vapor deposition, etc.).

In some embodiment, the plurality of metal interconnect layers 206 may be formed by selectively exposing the ILD layer 204 to an etchant configured to selectively etch the ILD layer 204 to form a plurality of openings. A metal material (e.g., tungsten, aluminum, and/or copper) is subsequently formed within the plurality of openings. In various embodiments, the etchant may comprise a dry etchant have an etching chemistry comprising a fluorine species (e.g., $CF_4$, $CHF_3$, $C_4F_8$, etc.) or a wet etchant comprising hydroflouric acid (HF), for example.

Figure 11:
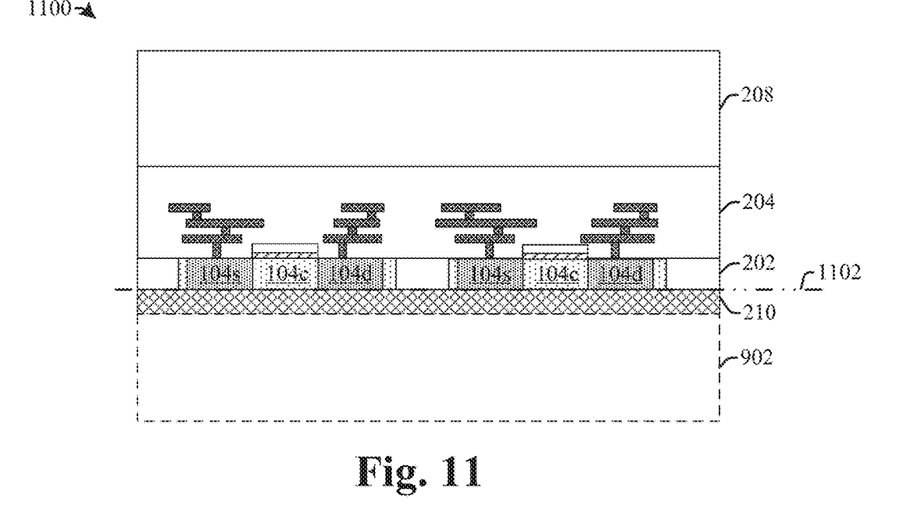

FIG. 11 illustrates a cross-sectional view 1100 of an integrated chip corresponding to acts 806-808.

As shown in cross-sectional view 1100, the first handle substrate 902 is removed and the ILD layer 204 is bonded to a second handle substrate 208 (i.e., a carrier substrate) configured to provide support to the integrated chip. In some embodiments, a part of a whole of the buried oxide layer 210 may also be removed. In some embodiments, the first handle substrate 902 and the buried oxide layer 210 may be removed by a chemical mechanical polishing (CMP) process (along line 1102) or by an etching process. In some embodiments, the buried oxide layer 210 may be left over the source region 104s and drain region 104d, but is removed from over the channel region 104c. In such embodiments, the buried oxide layer 210 may increase the sensitivity of the transistor device 104 to optical signals by limit photons hitting the source region 104s and drain region 104d.

Figure 12:
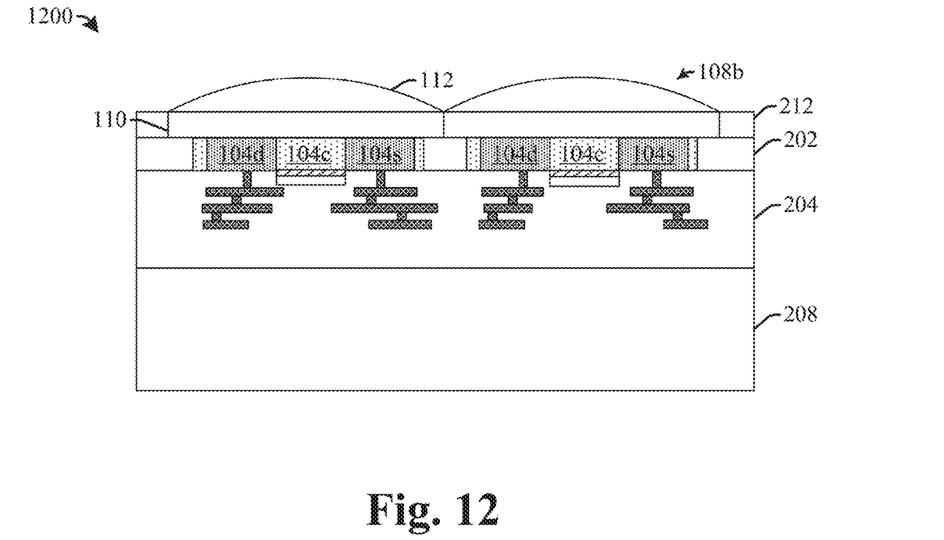

FIG. 12 illustrates some embodiments of a cross-sectional view 1200 of an integrated chip corresponding to acts 810-812.

As shown in cross-sectional view 1200, color filters 110 are formed. In some embodiments, the color filters 110 may be formed onto the active silicon layer 202. In other embodiments, the color filters may alternatively or additionally be formed onto the buried oxide layer (e.g., 210 of FIG. 11). In some embodiments, the one or more color filters 110 may be formed by a depositing a material and then separately patterning the material to form different color filters.

Micro-lenses 112 are formed over the color filters 110. In some embodiments, the micro-lenses 112 may be formed by depositing a micro-lens material above the color filters 110 (e.g., by a spin-on method or a deposition process). A micro-lens template (not shown) having a curved upper surface is patterned above the micro-lens material. In some embodiments, the micro-lens template may comprise a photoresist material exposed using a distributing exposing light dose (e.g., for a negative photoresist more light is exposed at a bottom of the curvature and less light is exposed at a top of the curvature), developed and baked to form a rounding shape. The micro-lenses 112 are then formed by selectively etching the micro-lens material according to the micro-lens template.

Figure 13:
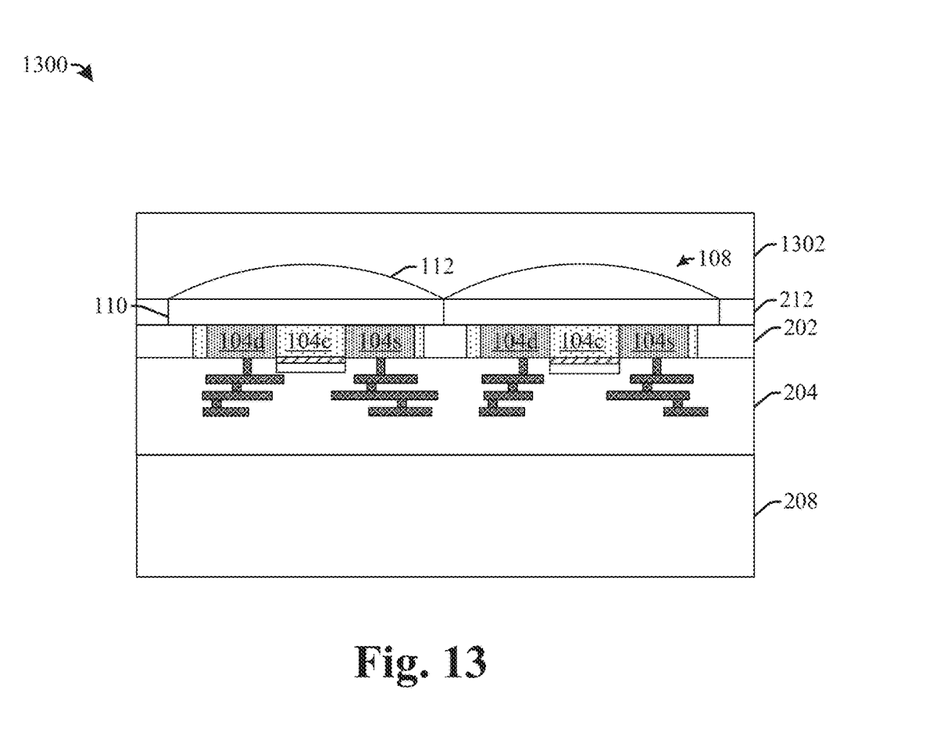

FIG. 13 illustrates some embodiments of a cross-sectional view 1300 of an integrated chip corresponding to act 814.

As shown in cross-sectional view 1300, a first dielectric layer 1302 is formed over the micro-lenses 112. In some embodiments, the first dielectric layer 1302 may comprise silicon dioxide (SiO2). The first dielectric layer 1302 may be deposited by way of a vapor deposition process (e.g., PVD, ALD, CVD, PE-CVD).

Figure 14A:
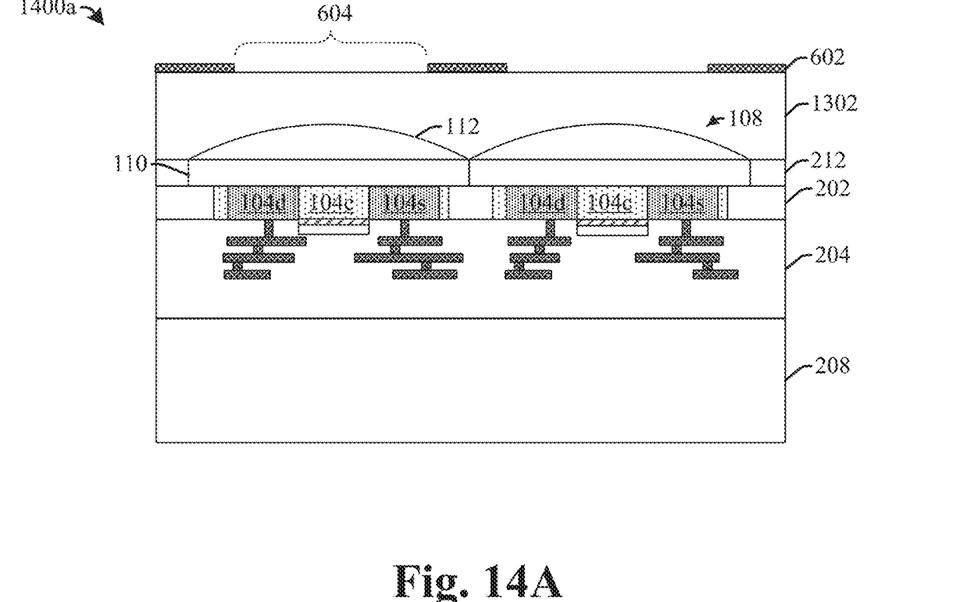

FIG. 14A illustrates some embodiments of a cross-sectional view 1400a of an integrated chip corresponding to act 818.

As shown in cross-sectional view 1400a, one or more electrodes 602 are formed over the first dielectric layer 1302, in some embodiments. The one or more electrodes 602 may comprise a conductive material such as aluminum, copper, or a combination thereof. The one or more electrodes 602 may be formed by depositing the conductive material onto the first dielectric layer 1302 and by selectively patterning the conductive material to define the one or more electrodes 602. In some embodiments, the one or more electrodes 602 may be patterned to form openings 604 overlying the micro-lenses 112.

Figure 14B:
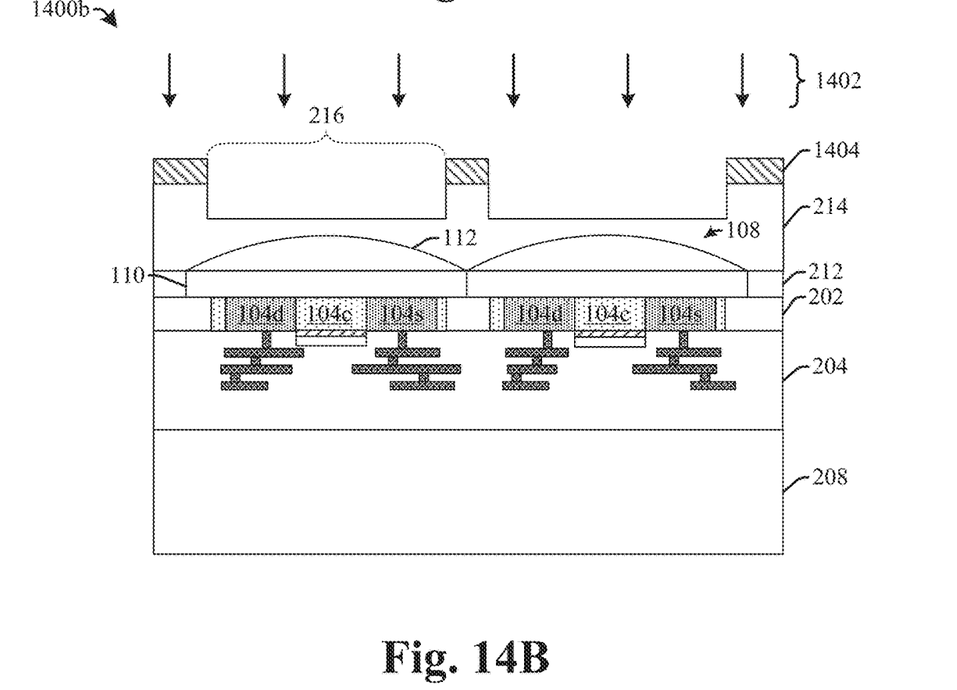

FIG. 14B illustrates some embodiments of a cross-sectional view 1200 of an integrated chip corresponding to act 816.

As shown in cross-sectional view 1400b, a masking layer 1404 is selectively formed over the first dielectric layer 214. The masking layer 1404 defines a position of recesses 216 within the first dielectric layer 214. In some embodiments, the masking layer 1404 may comprise a photoresist layer patterned according to a photolithography process. In other embodiments, the masking layer 1404 may comprise a hardmask layer (e.g., SiN) patterned according to a dry etching process (e.g., having an etching chemistry comprising $CF_4$, $CHF_3$, $C_4F_8$, HF, etc.). The first dielectric layer 214 is selectively exposed to an etchant 1402 configured to selectively etch the first dielectric layer 214 according to the masking layer 1404. In some embodiments, the etchant 1402 may comprise a dry etchant (e.g., having an etching chemistry comprising $CF_4$, $CHF_3$, $C_4F_8$, HF, etc.). In other embodiments, the etchant 1402 may comprise a wet etchant (e.g., a buffered hydroflouric (HF) acid solution).

Figure 15:
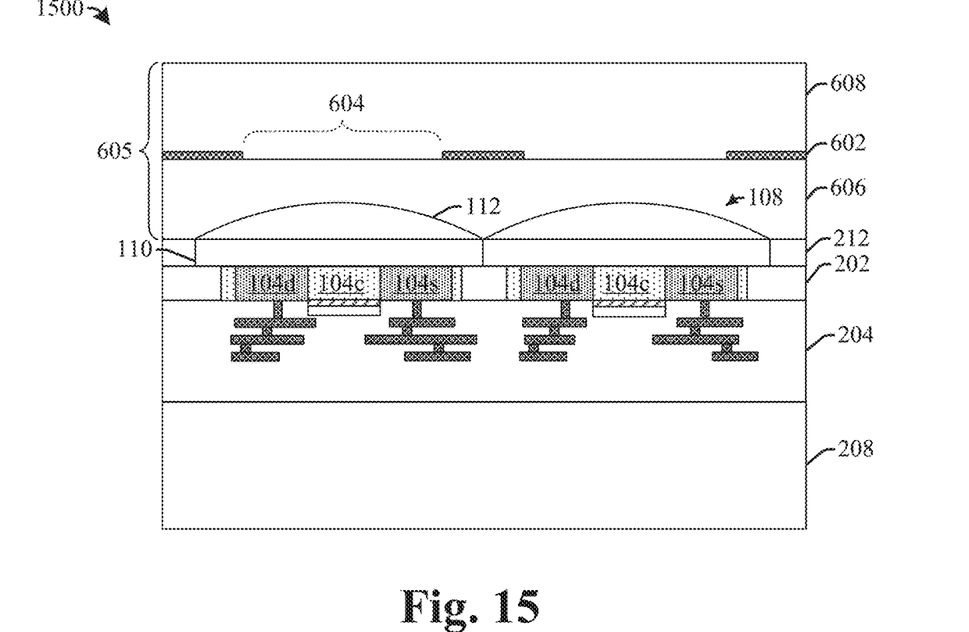

FIG. 15 illustrates some embodiments of a cross-sectional view 1500 of an integrated chip corresponding to act 820.

As shown in cross-sectional view 1500, a second dielectric layer 608 is disposed over the one or more electrodes 602 and the first dielectric layer 606. In some embodiments, the second dielectric layer 608 may comprise a same dielectric material as the first dielectric layer 606. In other embodiments, the first dielectric layer 606 and the second dielectric layer 608 may comprise different dielectric materials. In some embodiments, the first dielectric layer 606 and the second dielectric layer 608 may comprise silicon dioxide (SiO2). The second dielectric layer 608 may be deposited by way of a vapor deposition process (e.g., PVD, ALD, CVD, PE-CVD).

Figure 16:
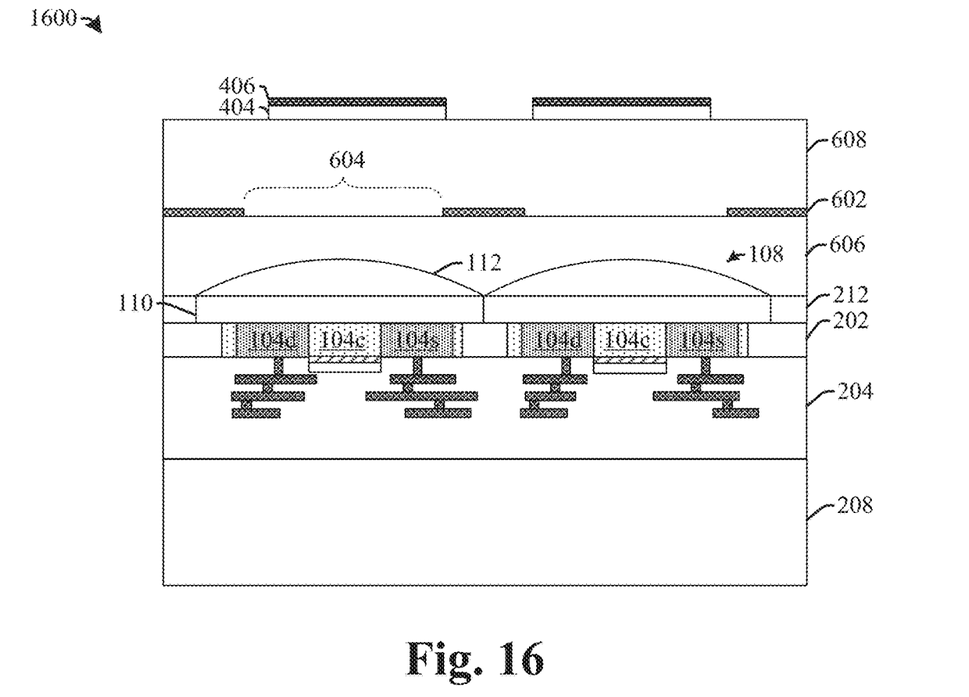

FIG. 16 illustrates some embodiments of a cross-sectional view 1600 of an integrated chip corresponding to act 822.

As shown in cross-sectional view 1600, optical signal conduits 404 are formed onto the second dielectric layer 608. The optical signal conduits 404 may be formed by depositing an optically conductive material onto the second dielectric layer 608, and then patterning the optically conductive material. In some embodiments, the optically conductive material may be patterned using a dry etching process. In some embodiments, a reception layer 406 may be formed over the optical signal conduit 404. In some embodiments, the optically conductive material may comprise a high-k material such as silicon nitride (Si3N4), silicon oxynitride (SiON), hafnium dioxide (HfO2), tantalum pentoxide (Ta2O5), or the like having a thickness in a range of between approximately 500 angstroms and approximately 6000 angstroms. In some embodiments, the optically conductive material may be patterned to form the optical signal conduit 404 using a dry etching process.

Figure 17:
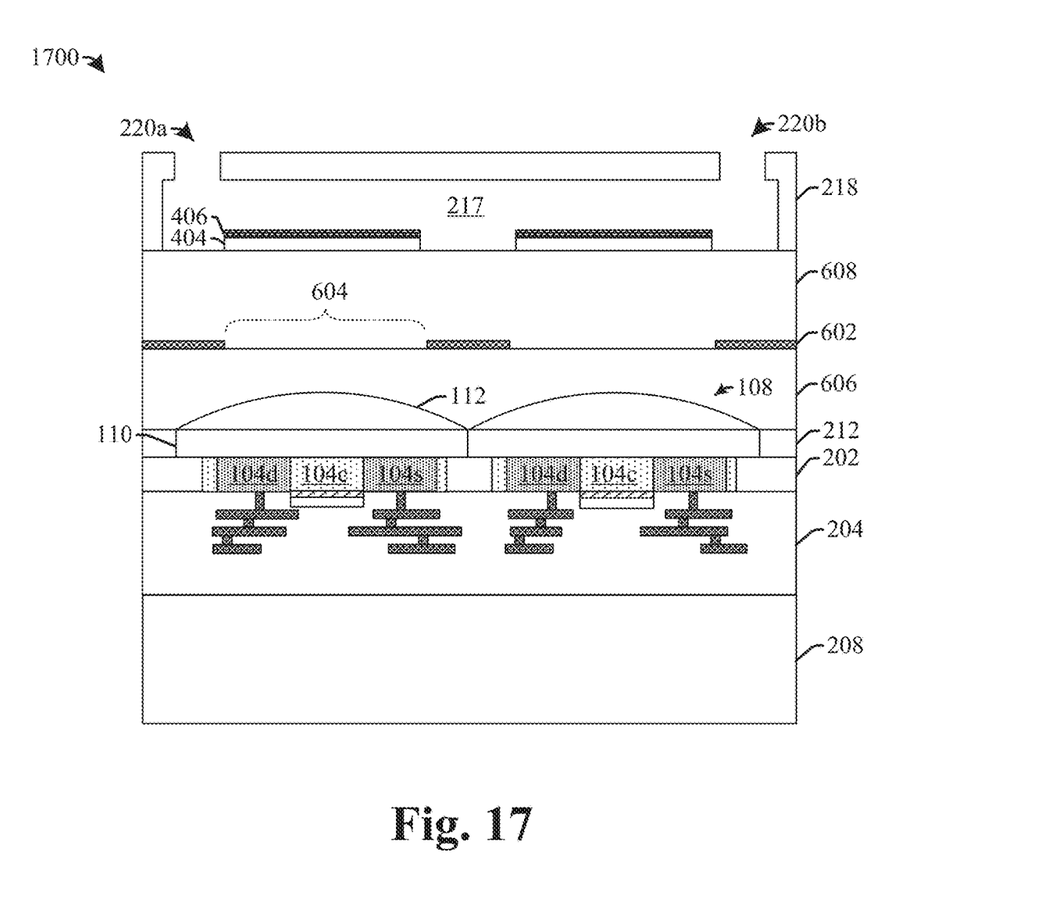

FIG. 17 illustrates some embodiments of a cross-sectional view 1700 of an integrated chip corresponding to act 824.

As shown in cross-sectional view 1600, capping structure 218 is disposed over the second dielectric layer 608. It will be appreciated that in embodiments wherein recesses are formed in the first dielectric layer (e.g., shown in FIG. 14B), the capping structure may alternatively be formed onto the first dielectric layer 214. The capping structure 218 forms a micro-fluidic chamber 217 over the second dielectric layer 608. In some embodiments, the capping structure 218 may comprise a polymer. The capping structure 218 may be formed by depositing the polymer (e.g., polydimethylsiloxane (PDMS)) onto a mold and then curing (e.g., heated at an elevated temperature) the polymer. The resulting capping structure 218 may be subsequently transferred to the second dielectric layer 608.

Therefore, the present disclosure relates to an integrated chip having an integrated optical bio-sensor with a relatively small form factor.

In some embodiments, the present disclosure relates to an integrated chip having an integrated optical bio-sensor. The integrated chip comprises a sensing device disposed within a semiconductor substrate. An optical waveguide structure is arranged over a first side of the semiconductor substrate at a position laterally overlying the sensing device. A dielectric structure disposed onto the optical waveguide structure at a position that separates the optical waveguide structure from a sample retention area configured to receive a sample solution.

In other embodiments, the present disclosure relates to an integrated chip having an integrated optical bio-sensor. The integrated chip comprises a transistor device disposed within an active silicon layer and having a source region and a drain region that are laterally separated by a channel region. The source region and the drain region vertically extend through the active silicon layer. A color filter is arranged over a first side of the active silicon layer and laterally aligned with the transistor device, and a micro-lens is arranged over the color filter. A dielectric structure is disposed onto the micro-lens at a position that separates the micro-lens from a sample retention area configured to receive a sample solution. A capping structure is arranged to abut the dielectric structure to form a micro-fluidic chamber arranged between the dielectric structure the capping structure.

In yet other embodiments, the present disclosure relates to a method of forming an integrated chip having an integrated optical bio-sensor. The method comprises forming a sensing device within a semiconductor substrate, and forming an optical waveguide structure over a first side of the semiconductor substrate at a position laterally overlying the sensing device. The method further comprises forming a dielectric structure onto the optical waveguide structure at a position that vertically separates the optical waveguide structure from a sample retention area configured to receive a sample solution.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An integrated chip having an integrated bio-sensor, comprising:
   an active silicon layer having a first side and a second side opposite the first side, the first side over the second side;
   a transistor device disposed within the active silicon layer and having a source region and a drain region that are separated by a channel region, wherein the source region and the drain region extend from the first side through the active silicon layer to the second side;
   a color filter arranged over the first side of the active silicon layer and aligned with the transistor device;
   a micro-lens having a lower surface and an upper surface and arranged over the color filter, wherein the lower surface is in contact with the color filter;
   a dielectric structure disposed over the micro-lens, wherein the upper surface of the micro-lens is in contact with the dielectric structure;
   a capping structure abutting the dielectric structure to form a micro-fluidic chamber arranged between the dielectric structure and the capping structure, wherein the dielectric structure separates the micro-lens from the micro-fluidic chamber; and
   wherein the micro-fluidic chamber is configured to hold a sample that generates photons in response to incident radiation, and wherein the photons are configured to travel through the dielectric structure to the micro-lens, through the micro-lens to the color filter, and through the color filter to the transistor device.

2. The integrated chip of claim 1, further comprising:
   a gate structure arranged along the second side of the active silicon layer opposite the first side of the active silicon layer, wherein the gate structure comprises a gate electrode and a gate dielectric with outermost sidewalls that are disposed along a line intersecting the second side of the active silicon layer; and
   a plurality of interconnect layers arranged within an inter-level dielectric (ILD) layer disposed along the second side of the active silicon layer.

3. The integrated chip of claim 1, further comprising:
   one or more electrodes comprising a conductive material, which are disposed within the dielectric structure, wherein the one or more electrodes are separated from the active silicon layer by the dielectric structure and have an opening overlying the micro-lens.

4. The integrated chip of claim 1, further comprising:
   a probe disposed onto the dielectric structure at a location overlying the micro-lens, wherein the probe is configured to immobilize a specific target bio-molecule.

5. An integrated chip, comprising:
   a transistor device disposed within a semiconductor substrate and having a source region and a drain region that are laterally separated by a channel region, wherein the source region and the drain region vertically extend through the semiconductor substrate;
   a color filter arranged over the transistor device along a first side of the semiconductor substrate;
   a micro-lens arranged over the color filter and separated from the transistor device by the color filter;
   a dielectric structure arranged over the micro-lens and separated from the color filter by the micro-lens;
   a capping structure arranged over the dielectric structure to define a micro-fluidic chamber arranged between the dielectric structure and the capping structure, wherein the dielectric structure separates the micro-lens from the micro-fluidic chamber; and
   wherein the micro-fluidic chamber is configured to hold a sample that generates photons in response to incident radiation, wherein the photons are configured to travel through the dielectric structure to the micro-lens, from the micro-lens to the color filter, and from the color filter to the transistor device, and wherein the photons are configured to generate a current within the channel region of the transistor device.

6. The integrated chip of claim 5,
   wherein the micro-lens has a curved surface facing away from the semiconductor substrate; and
   wherein the dielectric structure completely covers the curved surface of the micro-lens facing away from the semiconductor substrate.

7. The integrated chip of claim 5, further comprising:
   a second transistor device disposed within the semiconductor substrate and having a second source region and a second drain region that are laterally separated by a second channel region;
   a second color filter arranged over the second transistor device along the first side of the semiconductor substrate;
   a second micro-lens separated from the second transistor device by the second color filter; and wherein the dielectric structure is arranged over the second micro-lens, and the second micro-lens is between the second color filter and the dielectric structure.

8. An integrated chip, comprising:
a transistor device disposed within a semiconductor substrate and having a source region and a drain region that are laterally separated by a channel region, wherein the semiconductor substrate has a first side and a second side opposing the first side;
a color filter arranged directly over the transistor device, wherein the first side of the semiconductor substrate is between the color filter and the second side of the semiconductor substrate;
a micro-lens arranged directly over the color filter, wherein the micro-lens has a flat bottom surface facing the color filter and a curved upper surface;
a dielectric structure disposed onto the micro-lens, wherein the dielectric structure has interior sidewalls that define a recess within an upper surface of the dielectric structure directly over the micro-lens, and wherein the dielectric structure vertically separates the recess from the micro-lens;
a capping structure abutting the dielectric structure to define a micro-fluidic chamber arranged between the dielectric structure and the capping structure;
a plurality of metal interconnect layers arranged within an inter-level dielectric (ILD) structure disposed along the second side of the semiconductor substrate opposing the first side of the semiconductor substrate; and
wherein the micro-fluidic chamber is configured to hold a sample that generates photons in response to incident radiation, and wherein the photons are configured to travel through the dielectric structure prior to traveling through the micro-lens, and to travel through the micro-lens prior to traveling through the color filter.

9. The integrated chip of claim 8, wherein the dielectric structure has a surface continuously extending between bottoms of the interior sidewalls.

10. The integrated chip of claim 9, further comprising:
a probe disposed onto the surface between bottoms of the interior sidewalls at a location separated from the micro-lens by the dielectric structure, wherein the probe is configured to immobilize a specific target bio-molecule.

11. The integrated chip of claim 8, wherein the curved upper surface of the micro-lens directly contacts the dielectric structure.

12. The integrated chip of claim 8, wherein the dielectric structure completely covers the curved upper surface of the micro-lens.

13. The integrated chip of claim 8, wherein the micro-lens is arranged between the micro-fluidic chamber and the semiconductor substrate along a line that is perpendicular to the first side of the semiconductor substrate.

14. The integrated chip of claim 8, wherein the source region and the drain region vertically extend from the first side of the semiconductor substrate to the second side of the semiconductor substrate.

15. The integrated chip of claim 8, further comprising:
a buried oxide layer having a first side that contacts the semiconductor substrate and having a second side that faces an opposite direction as the first side and that contacts the color filter.

16. The integrated chip of claim 8, further comprising:
a photodiode or an avalanche photodiode arranged at a position between the color filter and the transistor device.

17. The integrated chip of claim 8, further comprising:
a second transistor device disposed within the semiconductor substrate and having a second source region and a second drain region that are laterally separated by a second channel region;
a second color filter arranged over the second transistor device along the first side of the semiconductor substrate;
a second micro-lens separated from the second transistor device by the second color filter; and
wherein the dielectric structure is arranged over the second micro-lens and is separated from the second color filter by the second micro-lens.

18. The integrated chip of claim 8, further comprising:
one or more optical signal conduits separated from the micro-lens by the dielectric structure, wherein the one or more optical signal conduits extend from a first position outside of the capping structure to a second position within the micro-fluidic chamber that overlies the transistor device.

19. The integrated chip of claim 18, further comprising:
one or more electrodes comprising a conductive material, which are disposed within the dielectric structure at a location vertically between the micro-lens and the optical signal conduits, wherein the one or more electrodes define an aperture overlying the micro-lens.

20. The integrated chip of claim 5, wherein the color filter is disposed between the micro-fluidic chamber and the transistor device along a line extending in a direction perpendicular to the first side of the semiconductor substrate.

* * * * *